(12) United States Patent
Miller, II

(10) Patent No.: US 10,161,847 B2
(45) Date of Patent: Dec. 25, 2018

(54) METHOD AND SYSTEM FOR DETECTING AN AIRBORNE TRIGGER

(71) Applicant: AT&T INTELLECTUAL PROPERTY I, L.P., Atlanta, GA (US)

(72) Inventor: Robert Raymond Miller, II, Convent Station, NJ (US)

(73) Assignee: AT&T INTELLECTUAL PROPERTY I, L.P., Atlanta, GA (US)

(*) Notice: Subject to any disclaimer, the term of this patent is extended or adjusted under 35 U.S.C. 154(b) by 0 days.

(21) Appl. No.: 16/026,592

(22) Filed: Jul. 3, 2018

(65) Prior Publication Data

US 2018/0328833 A1 Nov. 15, 2018

Related U.S. Application Data

(63) Continuation of application No. 14/988,432, filed on Jan. 5, 2016, now Pat. No. 10,036,696, which is a
(Continued)

(51) Int. Cl.
*G08B 21/00* (2006.01)
*G01N 15/10* (2006.01)
(Continued)

(52) U.S. Cl.
CPC .............. *G01N 15/10* (2013.01); *G01N 5/02* (2013.01); *G01N 15/06* (2013.01); *G01N 29/12* (2013.01);
(Continued)

(58) Field of Classification Search
CPC ...... G08B 17/10; G08B 17/107; G08B 17/11; G08B 21/14; G08B 21/182; G08B 29/185;
(Continued)

(56) References Cited

U.S. PATENT DOCUMENTS 7,382,125 B2 6/2008 Fisher et al.
7,454,314 B2 11/2008 Holland et al.
(Continued)

OTHER PUBLICATIONS

"ISO/IEEE 11073 Personal Health Data (PHD) Standards," <http://en.wikipedia.org/w/index.php?oldid=446538013>, retrieved Oct. 31, 2011, 16 pages.
(Continued)

*Primary Examiner* — Joseph Feild
*Assistant Examiner* — Sharmin Akhter
(74) *Attorney, Agent, or Firm* — Toler Law Group, PC

(57) ABSTRACT

A method includes receiving multiplexed sensor data from a sensor array. The multiplexed sensor data includes first data from a first sensor of the sensor array and second data from a second sensor of the sensory array. The first data includes first frequency information of a first cantilevered element, the first cantilevered element including a coating material having an affinity for a compound and no diffusion barrier. The second data includes second frequency information of a second cantilevered element, the second cantilevered element including the coating material and a diffusion barrier. The diffusion barrier inhibits mass transfer to the second cantilevered element. The method also includes conditionally generating, based on an analysis of the first data and the second data, an output. The output is conditioned on the first frequency information and the second frequency information indicating more than a threshold amount of the compound present at the sensor array.

20 Claims, 7 Drawing Sheets

Related U.S. Application Data continuation of application No. 14/303,386, filed on Jun. 12, 2014, now Pat. No. 9,261,488, which is a continuation of application No. 13/307,591, filed on Nov. 30, 2011, now Pat. No. 8,786,432.

(51) Int. Cl.

| | | |
|---|---|---|
| *G01N 29/44* | (2006.01) | |
| *G08B 21/12* | (2006.01) | |
| *G01N 5/02* | (2006.01) | |
| *G05D 19/02* | (2006.01) | |
| *G01N 29/12* | (2006.01) | |
| *G05B 15/02* | (2006.01) | |
| *G01N 15/06* | (2006.01) | |

(52) U.S. Cl.
CPC .............. *G01N 29/44* (2013.01); *G05B 15/02* (2013.01); *G05D 19/02* (2013.01); *G08B 21/12* (2013.01); *G01N 2291/02408* (2013.01)

(58) Field of Classification Search
CPC ........ G08B 3/10; G08B 17/00; G08B 17/103; G08B 13/08; G08B 13/1427; G08B 13/22; G08B 29/046
USPC ......... 340/540, 545.2, 545.4, 547, 561, 562, 340/566, 577–579, 628–630; 324/686
See application file for complete search history.

(56) References Cited

U.S. PATENT DOCUMENTS

| | | | |
|---|---|---|---|
| 7,761,106 B2 | 7/2010 | Konchitsky | |
| 7,774,852 B2 | 8/2010 | Yokota et al. | |
| 7,788,343 B2 | 8/2010 | Haselhurst et al. | |
| 7,831,408 B2 | 11/2010 | Petrucelli | |
| 7,840,694 B2 | 11/2010 | Yamaki | |
| 7,853,987 B2 | 12/2010 | Balasubramanian et al. | |
| 7,890,681 B2 | 2/2011 | Yung-Chang | |
| 7,910,789 B2 | 3/2011 | Sinyagin | |
| 7,911,345 B2 | 3/2011 | Potyrailo et al. | |
| 7,937,347 B2 | 5/2011 | Anerousis et al. | |
| 7,951,080 B2 | 5/2011 | Taub | |
| 7,978,062 B2 | 7/2011 | Lalonde et al. | |
| 7,980,998 B2 | 7/2011 | Shemesh et al. | |
| 7,984,327 B2 | 7/2011 | Winokur | |
| 2004/0041695 A1 | 3/2004 | Reining | |
| 2006/0257286 A1* | 11/2006 | Adams ................. | G01N 29/022 422/82.01 |
| 2008/0001735 A1 | 1/2008 | Tran | |
| 2008/0262743 A1 | 10/2008 | Lewis et al. | |
| 2009/0045967 A1 | 2/2009 | Bandholz et al. | |
| 2009/0253364 A1 | 10/2009 | Henry | |
| 2010/0010743 A1 | 1/2010 | Petrovic | |
| 2010/0161354 A1 | 6/2010 | Lim et al. | |
| 2010/0280796 A1 | 11/2010 | Ramin et al. | |
| 2011/0113855 A1* | 5/2011 | Badding ............... | G01N 29/022 73/24.06 |

OTHER PUBLICATIONS

"Health informatics—Personal health device communication—Part 10404: Device specialization—Pulse oximeter," International Standard, ISO/IEEE 11073-1040:2010(E), First edition, May 1, 2010, 80 pages.

"ISO/IEEE 11073," Health Informatics—Medical / Health Device Communication Standards, <http://en.wikipedia.org/w/index.php?oldid=458351880>, retrieved Oct. 7, 2011, 9 pages.

Clarke, M., "Developing a Standard for Personal Health Devices based on 11073," eHealth Beyond the Horizon—Get IT There, IOS Press, 2008, pp. 717-722.

\* cited by examiner

METHOD AND SYSTEM FOR DETECTING AN AIRBORNE TRIGGER

CLAIM OF PRIORITY

This application claims priority from, and is a continuation application of, U.S. patent application Ser. No. 14/988,432, filed Jan. 5, 2016, which is a continuation of U.S. patent application Ser. No. 14/303,386, filed Jun. 12, 2014, now issued as U.S. Pat. No. 9,261,488, which is a continuation application of U.S. patent application Ser. No. 13/307,591, filed Nov. 30, 2011, now issued as U.S. Pat. No. 8,786,432, the content of each of which is incorporated by reference herein in its entirety.

FIELD OF THE DISCLOSURE

The present disclosure is generally related to detecting sensor data associated with an airborne trigger.

BACKGROUND

Respiratory problems afflict a wide variety of individuals from children to seniors. For example, an individual may be diagnosed with asthma, allergies, or chronic obstructive pulmonary disease (COPD). An "attack" to the respiratory system of such an individual may negatively affect the health of the individual. Of particular concern are individuals living in confined environments, such as hospitals and nursing homes. Studies have shown that a "trigger" (e.g., an airborne trigger) may be instrumental in impeding (e.g., "attacking") an individual's respiratory functionality. In many situations, the trigger may go undetected or unidentified and a respiratory attack appears to occur at random. The trigger may be a compound such as dust, pollen, a chemical, or a volatile organic compound (VOCs) often found in a carpet, a wall covering, furniture, a cleaning supply product, a fragrance, an air freshener, or another source within a residence or other facility.

DETAILED DESCRIPTION

Figure 1:
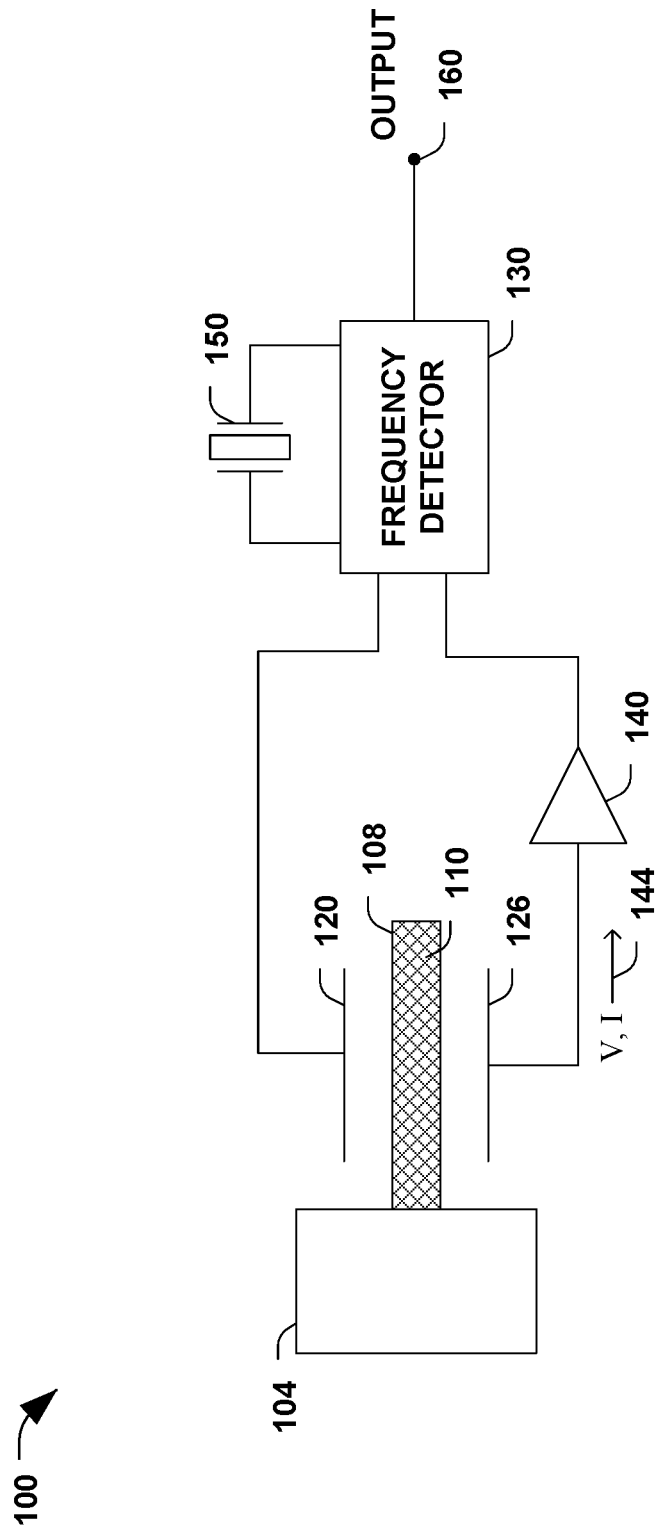
FIG. 1 is a diagram of a sensor configured to detect a particle of at least one compound.

A sensor may be used to detect the presence of triggers, such as airborne compounds, that may affect a respiratory system of an individual. The sensor may use metal-oxide semiconductor, field effect, piezoelectric, or quartz microbalance technologies. In a particular embodiment of the sensor, a particular sensor may utilize a combination of active devices with Micro-Electromechanical System (MEMS) technology. The particular sensor may be efficient, may be inexpensive to produce, and may return to a normal state quickly when a concentration of a target compound is reduced. The particular sensor may further include a resonator (e.g., a cantilevered element) that is used as part of an oscillator having a frequency determined by resonance of a crystal or silicon resonator (e.g., a "tuning fork"). The resonator may be coated with a material (e.g., a coating material) having an affinity for at least one compound associated with a trigger. The material may be adapted to couple to a particle of the at least one compound. When multiple particles of the at least one compound couple to the material in a sufficient quantity, the oscillator may change frequency in response to the additional mass, thereby changing the frequency of the oscillator. The sensor may provide sensor data associated with the frequency of the resonator, thereby indicating the presence of the at least one compound.

A sensor device may include multiple sensors where a first sensor is adapted to detect a presence of at least one compound that is not detected by a second sensor. In a particular embodiment, a group of sensors may correspond to a particular compound. Accordingly, the compound may be identified by each sensor of the group of sensors providing an indication that a corresponding particle of the compound is present. In another particular embodiment, a first sensor and a second sensor detect the same compound and a diffusion barrier at least partially shields the first sensor so that the first sensor detects a presence of a particle at a different rate than the second sensor detects the presence of the particle.

The sensor device may include a microcomputer to receive an output from each sensor of the sensor array. The microcomputer may convert the sensor output to digital data. The digital data may be transmitted in compliance with one or more of INSTITUTE OF ELECTRICAL AND ELECTRONICS ENGINEERS (IEEE) 11073 standards. The digital data may be transmitted from the sensor device via a wireless modem (e.g., a ZigBee device, a USB device, or a Bluetooth™ device). The digital data may be transmitted via a broadband connection (e.g., a digital subscriber line (DSL) connection) or via a cellular or other wireless connection and may be received by a server located in a network (e.g., a cloud). The server may include a database, analytics, and/or an alerting system.

The database may store the digital data (e.g., the sensor data) and the digital data may be made available to medical professionals (e.g., a caregiver, nurse, or doctor). The stored digital data may be interpreted or processed by the analytics which may identify and indicate a presence of a particular trigger. Based at least in part on identification of the particular trigger, an alerting system may generate an alert for an individual who may suffer a respiratory attack based on the particular trigger. The alert may be provided to a caregiver by a facility automation system that controls environmental characteristics (e.g., ventilation) of a facility.

A device (e.g., a sensor device) including a plurality of sensors may be used in a roaming capacity or placed (e.g., stationary) in a home, a managed care facility, a hospital, or another facility to relay sensor data to a "cloud." The device and companion analytics included in the cloud may identify the particular trigger and, in response to identification of the particular trigger, a targeted alert may be issued by an alert system. Additionally, the identification of the particular trigger may be provided to a building control and automation systems to provide an improved environment for medical and well-being monitoring. Thus, the device, companion analytics, and the alert system may provide detection of triggers and early notification to an individual.

In a particular embodiment, an apparatus includes a cantilevered element including a coating material having an affinity for at least one compound. The apparatus further includes a first capacitive plate spaced from and capacitively coupled to the cantilevered element. The first capacitive plate is configured to induce a vibration in the cantilevered element at a frequency related to a mass of the cantilevered element. The apparatus also includes a second capacitive plate spaced from and capacitively coupled to the cantilevered element and a frequency detector coupled to the second capacitive plate. The frequency detector is adapted to detect a change in vibrational frequency of the cantilevered element as a result of a particle of the at least one compound coupling to the coating material.

In another particular embodiment, a device includes a sensor array including a plurality of sensors, the plurality of sensors including at least a first sensor and a second sensor. The first sensor includes a first cantilevered element including a first coating material having an affinity for at least one first compound. The first sensor further includes a first capacitive plate spaced from and capacitively coupled to the first cantilevered element. The first capacitive plate is configured to induce a vibration in the first cantilevered element at a first frequency related to a first mass of the first cantilevered element. The first sensor also includes a second capacitive plate spaced from and capacitively coupled to the first cantilever. The first sensor further includes a first frequency detector coupled to the second capacitive plate. The first frequency detector is adapted to detect a first change in vibrational frequency of the first cantilevered element as a result of a first particle of the at least one first compound coupling to the first coating material.

In another particular embodiment, a method of communicating data includes sending an association request from a sensor device to a manager device. The method further includes detecting a presence of at least one compound at the sensor device based on a sensor of the sensor device. Detecting the presence of the at least one compound includes inducing a vibration in a cantilevered element via a first capacitive plate spaced from and capacitively coupled to the cantilevered element. The cantilevered element includes a coating material having an affinity for the at least one compound and the vibration is related to a mass of the cantilevered element. Detecting the presence of the compound further includes providing an indication having a frequency associated with a vibrational frequency of the cantilevered element via a second capacitive plate. The second capacitive plate is spaced from and capacitively coupled to the cantilevered element. Detecting the presence of the compound includes detecting a change in the vibrational frequency of the cantilevered element at a frequency detector based on the indication. The frequency detector is coupled to the second capacitive plate and the change in the vibrational frequency results from a particle of the at least one compound coupling to the coating material. The method further includes transmitting sensor data associated with the detected presence of the at least one compound to the manager device.

FIG. 1 is a diagram illustrating a particular embodiment of a sensor 100 configured to detect a particle of at least one compound. The at least one compound may be a trigger that is associated with instances of respiratory attacks. The sensor 100 may include a fixed device, such as a microelectromechanical system (MEMS) technology component 104 (e.g., a silicon chip), a cantilevered element 108, a first capacitive plate 120, a second capacitive plate 126, a frequency detector, such as a frequency counter 130, an amplifier 140, a frequency reference component 150, and an output 160.

The cantilevered element 108 may be coupled to the MEMS technology component 104 at one end of the cantilevered element 108. The cantilevered element 108 may be silicon based and may be formed as part of an etching process in conjunction with manufacturing of the MEMS technology component 104. The cantilevered element 108 may be fixed to the MEMS technology component 104 at a first end of the cantilevered element 108 such that a second end of the cantilevered element 108, opposite the first end of the cantilevered element 108, is free to vibrate (e.g., oscillate). The cantilevered element 108 may have a natural resonance frequency with which the cantilevered element 108 vibrates. The natural resonance frequency may be determined based on a mass and dimensions of the cantilevered element 108.

The cantilevered element 108 may be coated with a material 110 (e.g., a coating material) as indicated by the crosshatched area of the cantilevered element 108 depicted in FIG. 1. The material 110 may cover the entire cantilevered element 108 or a portion of the cantilevered element 108. The material 110 may have an affinity for at least one compound. For example, the material 110 may be configured to attract and/or bind (physically or chemically) a particle of the at least one compound which is desired to be measured. The cantilevered element 108 including the material 110 may have a natural resonance frequency with which the cantilevered element 108 including the material 110 vibrates (e.g., oscillates). The at least one compound to be measured may be a trigger that impedes respiratory functions. When the at least one compound to be measured is present in the atmosphere (e.g., air) proximate to the sensor 100, particles of the at least one compound to be measured may couple to the material 110, thereby adding mass to the cantilevered element 108. As the mass of the cantilevered element 108 increases, the vibrational frequency of the cantilevered element 108 may change. Likewise, as the particles bound to the material 110 dissipate, the mass of the cantilevered element 108 decreases and the vibrational frequency of the cantilevered element 108 may also change. It may be understood that the mass of the cantilevered element 108 may be considered to be a mass of the cantilever element 108 and any additional mass coupled to the cantilever element 108 that may affect the vibrational frequency of the cantilevered element 108.

The cantilevered element 108 may be positioned between and proximate to the first capacitive plate 120 and the second capacitive plate 126. Each of the first capacitive plate 120 and the second capacitive plate 126 may be spaced from and capacitively coupled to the cantilevered element 108. Additionally, each of the first capacitive plate 120 and the second capacitive plate 126 may be spaced from the MEMS technology component 104.

The first capacitive plate 120 may be charged, responsive to a signal applied to the first capacitive plate 120, to attract or repel the cantilevered element 108. As a result of the signal applied to the first capacitive plate 120, the first capacitive plate 120 may induce (e.g., capacitively drive) the cantilevered element 108 to vibrate. The cantilevered element 108 may be free to vibrate without contacting the first capacitive plate 120 and/or without contacting the second capacitive plate 126. The second capacitive plate 126 may be configured to provide an indication (e.g., a voltage (V) and/or a current (I)) 144 having a frequency associated with a vibration of the cantilevered element 108. For example, as a concentration of a particular compound increases proximate to the sensor 100, more particles associated with the particular compound may couple to the cantilevered element 108. Thus, the indication 144 may indicate a presence, a concentration, or both of the compound.

The first capacitive plate 120 may be coupled to the frequency counter 130. The frequency counter 130 may be configured to provide the signal to the first capacitive plate 120. The second capacitive plate 126 may also be coupled to the frequency counter 130 via an amplifier 140. The amplifier 140 may amplify the indication 144 provided by the second capacitive plate 126. The amplifier 140 may provide the amplified indication having a frequency associated with the vibration of the cantilevered element 108 to the frequency counter 130.

In a particular embodiment, the frequency counter 130 may be adapted to detect a change in vibrational frequency of the cantilevered element 108 as a result of a particle of the at least one compound coupling to the material 110. In another particular embodiment, the frequency counter 130 may be configured to measure the frequency of the indication 144 (or the amplified indication provided from the amplifier 140). The frequency counter 130 may be further configured to determine a value associated with the measured frequency of the indication 144. The frequency counter 130 may also be configured to detect a change in the frequency of indication 144 (or the amplified indication provided from the amplifier 140) and to determine a value associated with the detected change in the frequency of the indication 144. The frequency counter 130 may be configured to provide an output 160 based at least in part on the value associated with the measured frequency or the value associated with the detected change in the frequency. The output 160 may be represented as an analog voltage, an analog current, an encoded signal, a current level, a voltage level, or by another electrical parameter.

The frequency counter 130 may be coupled to the frequency reference component 150 that resonates at a predetermined frequency. The frequency reference component 150 may include a quartz crystal. The frequency counter 130 may be configured to detect the predetermined frequency of the frequency reference component 150. The frequency counter 130 may be configured to determine the value associated the detected change in the frequency of the indication 144 based at least in part on the detected predetermined frequency of the frequency reference component 150.

Figure 2:
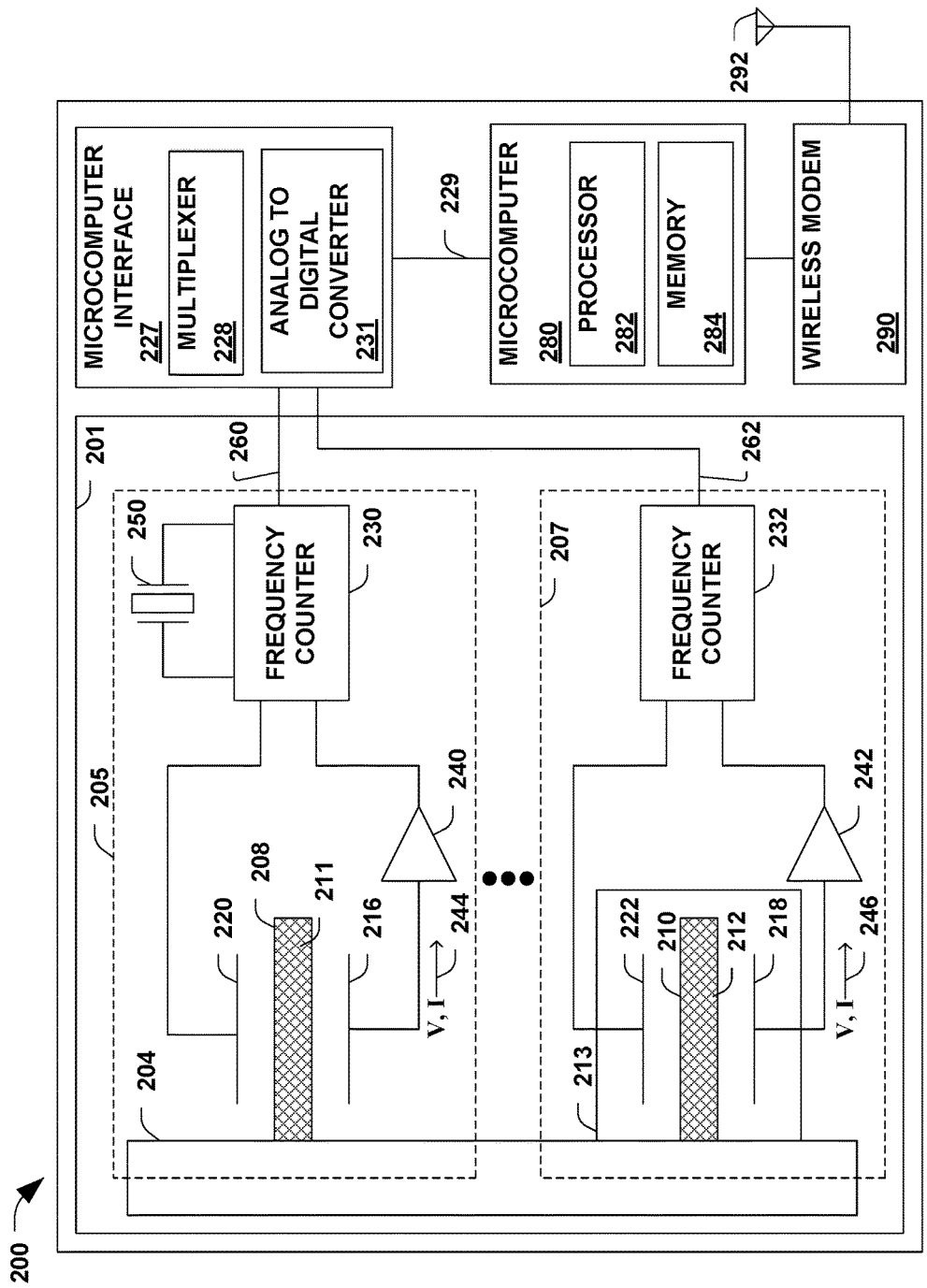
FIG. 2 is a diagram of a sensor device including a sensor array having sensors configured to detect one or more triggers.

FIG. 2 is a diagram of a sensor device 200 that includes a sensor array 201 having sensors configured to detect one or more triggers. The sensor array 201 may include a fixed device, such as a micro-electromechanical system (MEMS) technology component 204 (e.g., a silicon chip) and a plurality of sensors including at least a first sensor 205 and a second sensor 207. Each sensor of the sensor array 201 may be a particular implementation of the sensor 100 of FIG. 1, as described above. The sensor device 200 may further include a microcomputer interface 227, a microcomputer 280, a wireless modem 290, an antenna 292, or a combination thereof.

The first sensor 205 may include a first portion of the MEMS technology component 204, a first cantilevered element 208, a first capacitive plate 220, a second capacitive plate 216, a first frequency counter 230, a first amplifier 240, a frequency reference component 250, and a first output 260. The first capacitive plate 220 may induce the first cantilevered element 208 to vibrate and the second capacitive plate 216 may provide an indication (e.g., a voltage (V) and/or a current (I)) 244 having a frequency associated with a vibrational frequency of the first cantilevered element 208. The first sensor 205 may also include a first material 211 (e.g., a first coating material), as indicated by the crosshatched area of the first cantilevered element 208, that covers (e.g., coats) at least a portion of the first cantilevered element 208. The first sensor 205 may provide the first output 260 via the first frequency counter 230. The first output 260 may be associated with a vibrational frequency of the first cantilevered element 208. For example, the first output 260 may indicate a presence, absence, or concentration of a particular compound or set of compounds.

The second sensor 207 may include a second portion of the MEMS technology component 204, a second cantilevered element 210, a third capacitive plate 222, a fourth capacitive plate 218, a second frequency counter 232, a second amplifier 242, and a second output 262. The third capacitive plate 222 may induce the second cantilevered element 210 to vibrate and the fourth capacitive plate 218 may provide an indication (e.g., a voltage (V) and/or a current (I)) 246 having a frequency associated with a vibrational frequency of the second cantilevered element 210. The second sensor 207 may also include a second material 212 (e.g., a second coating material), as indicated by the crosshatched area of the second cantilevered element 210, that covers at least a portion of the second cantilevered element 210. The second sensor 207 may provide the second output 262 via the second frequency counter 232. The second output 262 may be associated with the vibrational frequency of the second cantilevered element 210. The second sensor 207 may include a corresponding frequency reference component (not shown) or may be coupled to the frequency reference component 250 included in the first sensor 205.

In a particular embodiment a diffusion barrier 213 (e.g., a porous medium) may cover at least a portion of the second sensor 207. For example, the diffusion barrier 213 may at least partially shield the second sensor 207. The diffusion barrier 213 may be configured to inhibit (e.g., slow down) particles (e.g., molecules) of one or more compounds from reaching the second material 212. Thus, the second sensor 207 shielded by the diffusion barrier 213 may detect a presence of a particular molecule type at a different rate (e.g., a slower rate) than when the second sensor 207 does not include the diffusion barrier 213.

In a particular embodiment, the first material 211 of the first sensor 205 and the second material 212 of the second sensor 207 may be different from one another. Each material 211, 212 may have an affinity for at least one corresponding compound. For example, in a particular embodiment, the first material 211 may have an affinity for at least one first compound and the second material 212 may have an affinity for at least one second compound. In a particular embodiment, the first material 211 and the second material 212 are different materials and the first coating material has an affinity for a particular compound included in the at least one first compound that is not included in the at least one second compound.

In another particular embodiment, the first material 211 of the first sensor 205 and the second material 212 of the second sensor 207 may be the same. In this embodiment, the second sensor 207 may include the diffusion barrier 213. Accordingly, the second sensor 207 may detect a presence of the at least one second compound at a slower rate than the first sensor 205 detects the presence of the at least one first compound. The use of two sensors having the same material, where one sensor is partially shielded from the atmosphere by the diffusion barrier 213, may enable the sensor device 200, or another device remotely located from the sensor device 200, to account for effects of temperature, improve an accuracy of readings, and reduce false readings. Additionally or in an alternative embodiment, the use of the two sensors having the same material, where one sensor is partially shielded by the diffusion barrier 213, may enable the sensor device 200, or another device remotely located from the sensor device 200, to differentiate between a steady state concentration (e.g., a background concentration) of a particular compound from a spike in a concentration of the particular compound.

Each sensor of the sensor array 201 may be coupled to the microcomputer interface 227. The microcomputer interface 227 may include a multiplexer 228 and an analog to digital converter 231 (e.g., an A/D converter). The microcomputer interface 227 may be configured to receive the first output 260 from the first sensor 205 and the second output 262 from the second sensor 207. In a particular embodiment, the microcomputer interface 227 may be configured to multiplex each output received from each sensor of the sensor array 201 to generate a multiplexed output. The analog to digital converter 231 may convert the multiplexed output to provide a digital output 229. In another particular embodiment, the analog to digital converter 231 converts each output received from each sensor of the sensor array 201 to a corresponding digital value and the multiplexer 228 multiplexes each corresponding digital value to generate the digital output 229.

The microcomputer interface 227 may be coupled to the microcomputer 280. The microcomputer 280 may include a processor 282 and a memory 284. The memory 284 may store instructions, executable by the processor 282, that enable the sensor device 200 to operate. The processor 282 may be configured to process the digital output 229 for transmission via the wireless modem 290 and the antenna 292 to a remote device. The microcomputer 280 may be configured to format the digital output 229 or to structure a data packet, based on the digital output 229, in compliance with one or more of the IEEE 11073 standards.

The wireless modem 290 may be coupled to the microcomputer 280 and to the antenna 292. The wireless modem 290 may be configured to transmit data associated with each sensor of the sensor array 201. For example, the wireless modem 290 may be configured to transmit data associated with a vibrational frequency of the first cantilevered element 208, data associated with a vibrational frequency of the second cantilevered element 210, or a combination thereof. In a particular embodiment, the wireless modem 290 may be configured to transmit a data packet based at least in part on the digital output 229 and configured by the microcomputer 280 in compliance with one or more of the IEEE 11073 standards.

Figure 3:
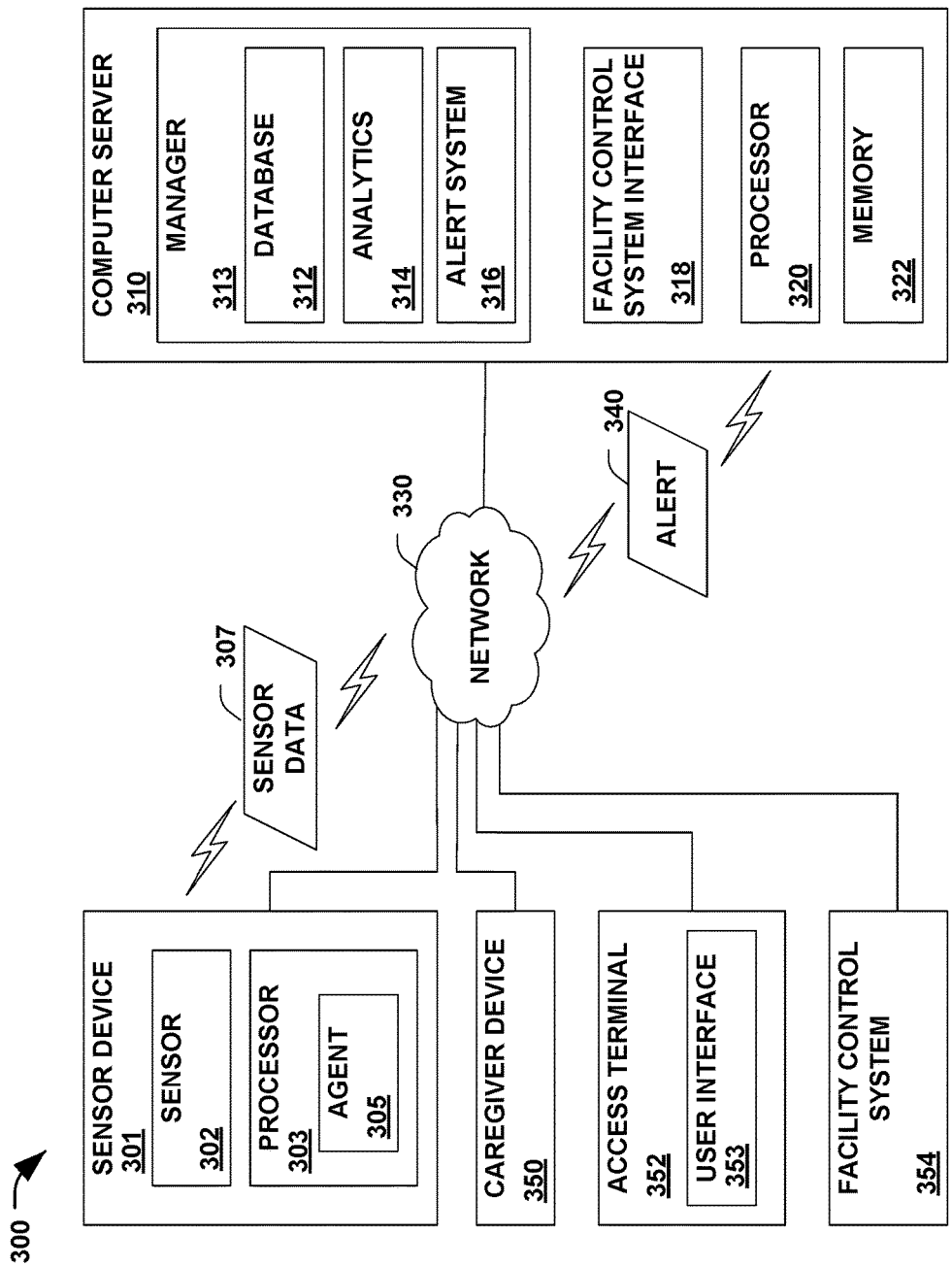
FIG. 3 is a diagram of a system including a sensor device and a manager, the system configured to detect and identify one or more triggers.

Referring to FIG. 3, a particular illustrative embodiment of a system 300 is shown. The system 300 may be configured to detect one or more triggers. The system 300 may include at least one sensor device 301, a computer server 310, a caregiver device 350, an access terminal 352, a facility control system 354, or a combination thereof, coupled via a network 330.

The network 330 may be implemented as a single network, a plurality of networks, or a combination thereof. In a particular embodiment, the network 330 may be a distributed computer network, such as a public computer network, or may be a private network and may be wireline, wireless, or a combination thereof.

The sensor device 301 may include a processor 303 and a representative sensor 302. The sensor device 301 may be a stationary device associated with a fixed location or may be a mobile device. When the sensor device 301 is a mobile device, the sensor device 301 may include components to determine a real-time position of the sensor device 301. During operation, the sensor device 301 may generate sensor data 307 based at least in part on a presence or concentration of a particle associated with at least one compound detected by the sensor 302. The sensor data 307 may also include additional information such as a timestamp, units of measure, a sensor device identification, individual sensor identification, location or position data, alarm data, flags, etc. In a particular illustrative embodiment, the sensor device 301 may be the sensor device 200 of FIG. 2 and the sensor 302 may be the sensor 100 of FIG. 1 or a sensor of the sensor array 201 of FIG. 2, as described above. Additionally, the sensor data 307 may be representative of the output 160 of the sensor 100 of FIG. 1 or at least one of the outputs 260, 262 of the sensor array 201 of FIG. 2, as described.

The processor 303 may execute an agent 305 associated with the sensor device 301. The agent 305 may include a configuration which represents the agent 305 as a set of objects using a domain information model. Each object may include one or more attributes to describe measurement data to be communicated and elements that control behavior and report on a status of the agent 305. In a particular embodiment, each object and each object's corresponding attributes may be defined using abstract syntax notation one (ASN.1).

The sensor device 301 may generate the sensor data 307 based on performing an evaluation of signals generated by the sensor 302. The sensor data 307 may be communicated via the network 330 to the computer server 310. In a particular embodiment, the computer server 310 may be remotely located from the sensor device 301. While only a single sensor device 301 is shown in FIG. 3, it should be understood that a plurality of different sensory devices may be coupled to the computer server 310 via the network 330. Additionally, the plurality of different sensory devices may be coupled directly or indirectly to the computer server 310 via the network 330 using a wired or wireless connection. Thus, the computer server 310 may receive, process, aggregate, and store sensor data from a plurality of different sensor devices.

The computer server 310 may include a manager 313, a facility control system interface 318, a processor 320, and a memory 322. The memory 322 may be coupled to the processor 320 in order to enable the processor 320 to execute a plurality of instructions from the memory 322. For example, the instructions may include operational instructions associated with the manager 313. Alternatively, the manager 313 may be implemented as a separate processor or a separate component within the computer server 310.

The manager 313 may include a database 312, analytics 314, an alert system 316, or a combination thereof. Upon receiving the sensor data 307, the manager 313 may store the sensor data 307 in the database 312. The manager 313 may be configured to perform one or more analytics 314 on the sensor data 307 before or after the sensor data 307 is stored in the database 312. In a particular embodiment, the computer server 310 may be associated with a particular facility, and the sensor data 307 may be forwarded to a remote server including a manager, such as the manager 313. The remote server may collect or receive data from a plurality of facilities as well as individual sensors that are not associated with the particular facility.

The database 312 may also store data identifying a particular sensor such as configuration data associated with the particular sensor or location information. The database 312 may also store data associated with a particular individual such as name, contact number, location, triggers known to induce a respiratory attack, sensitivity (e.g., severity of a reaction) to individual triggers, and a corresponding sensor identification number. The database 312 may further store data associated with a caregiver or facility including corresponding sensor identification numbers. The database 312 may also store data identifying which combination of molecule types (e.g., a particle) identifies a particular compound (e.g., a chemical or a chemical compound). For example, a group of sensors (each corresponding to a particular molecule type or a particular particle) of a plurality of sensors may correspond to a particular trigger (e.g., a particular chemical, a particular group of chemicals, or a class of chemicals, such as volatile organic compounds (VOCs)). The database 312 may store data identifying each sensor of the group of sensors and/or data correlating the group of sensors to the particular trigger. Thus, when the sensor data 307 identifies that each sensor of the group of sensors is indicating a presence of a corresponding particle, the database 312 may be utilized by the analytics 314 to determine that the particular trigger that corresponds to the group of sensors is present at a location proximate to the group of sensors.

The analytics 314 may perform an analysis of the sensor data 307 prior to or subsequent to storage of the sensor data 307 in the database 312. The analytics 314 may compare the sensor data 307 to thresholds or may evaluate the sensor data 307 in conjunction with either static data or data associated with different sensors. By comparing the sensor data 307 to the thresholds or by other similar mechanisms, the analytics 314 may identify particles and/or compounds associated with one or more triggers and may provide data associated with identification of the one or more triggers. The data may be provided to the alert system 316, the manager 313, or both.

Based on the identified particles and/or compounds associated with the one or more triggers, the manager 313 may execute or otherwise activate the alert system 316. The alert system 316 may issue an alert 340 based at least on the sensor data 307. For example, when the alert system 316 receives the data from the analytics 314, the alert system 316 may issue the alert 340. The alert 340 may include information indicating a compound type (e.g., a particular trigger), a concentration of the compound type, a location associated with the sensor device 301 associated with the compound type, a threat level associated with the compound type.

The alert 340 may be provided via the network 330 to a remote device such as the sensor device 301, the caregiver device 350, the access terminal 352, or the facility control system 354. The remote device may be implemented as a mobile communication device, a smart phone, a set-top box, or a personal computer (PC) such as a laptop, stationary computer, tablet PC, a personal digital assistant (PDA), a palmtop computer, a laptop computer, a desktop computer, a communications device, or a web appliance. The remote device may also include a display, a speaker, or a user interface, such as a user interface 353 of the access terminal 352. The remote device may be configure to vibrate, generate an audio signal (e.g., a special tone or message), display a message (e.g., a textual message, a pictorial message, or both), or a combination thereof. The remote device may vibrate, generate the audio signal, or display the message based at least in part on the alert 340. In response to receiving the alert 340, the remote device or an operator of the remote device may process the alert 340 and may perform one or more corrective or preventative actions associated with a detected trigger.

In a particular embodiment, the access terminal 352 may be operative to control the computer server 310. The access terminal 352 may include the user interface 353 that enable an operator of the access terminal to control the computer server 310. Controlling the computer server 310 may include accessing the manager 313, accessing, editing, or generating data stored in the database 312, accessing, editing, or generating parameters, algorithms, or settings associated with the analytics 314, and defining parameters of the alert system 316.

The facility control system interface 318 of the computer server 310 may be responsive to the analytics 314, the alert system 316, or both. The facility control system interface 318 may receive an indication that a trigger is detected and may process data included in the indication. The facility control system interface 318 may be configured to issue one or more commands to the facility control system 354 responsive to the indication. The one or more commands may enable the facility control system 354 to control various systems or equipment associated with a building or facility. For example, the systems or equipment may include a ventilation system, a sprinkler system, a security system, a pump, a fan, etc.

During operation of the system 300, the sensor device 301 may collect data, such as the sensor data 307, and transmit the sensor data 307 to the computer server 310 via the network 330. The manager 313 of the computer server 310 may receive the sensor data 307 and store the sensor data 307 in the database 312. The analytics 314 may perform an analysis of the sensor data 307 and determine that the sensor device 301 detected one or more compounds of interest (e.g., one or more compounds known to be or suspected to be a trigger for respiratory events). In response to the analytics 314 identifying a presence of the trigger, the alert system 316 may provide the alert 340 to at least one of the sensor device 301, the caregiver device 350, and the access terminal 352. The alert system 316 may also provide an indicator of the trigger including a location of the sensor device 301 to the facility control system interface 318. In response to the indicator, the facility control system interface 318 may issue a command to the facility control system 354 enabling the facility control system 354 to activate a ventilation system at a location associated with the sensor device 301 in order to dissipate the trigger from an environment surrounding sensor device 301.

Figure 4:
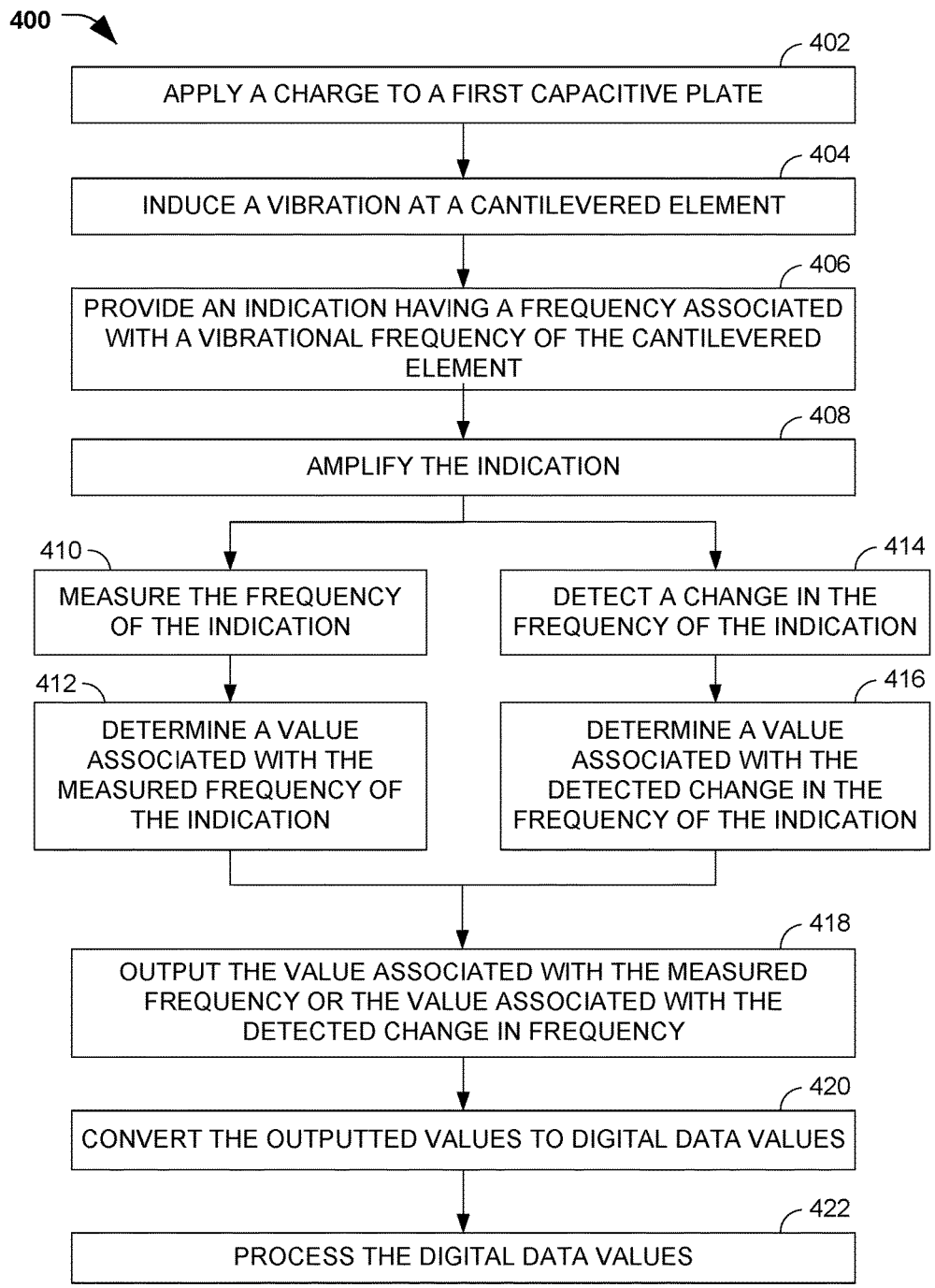
FIG. 4 is a flowchart to illustrate a method of operating a sensor configured to detect a particle of at least one compound.

Referring to FIG. 4, a method 400 of operating a sensor and/or sensor device is shown. The method 400 may include applying a charge to a first capacitive plate, at 402. For example, the first capacitive plate may be the first capacitive plate 120 of FIG. 1, the first capacitive plate 220 of FIG. 2, or the third capacitive plate 222 of FIG. 2, as described above.

The method 400 may include inducing a vibration at a cantilevered element, at 404. The vibration may be induced via electrical field effects by the charge applied to the first capacitive plate which may be spaced from and capacitively coupled to the cantilevered element. For example, the vibration may be induced at the cantilevered element 108 of FIG. 1, the cantilevered element 208 of FIG. 2, or the cantilevered element 210 of FIG. 2, as described above. The vibration may be related to a mass of the cantilevered element. The cantilevered element may include a coating material having an affinity for at least one compound.

The method may also include providing an indication having a frequency associated with a vibrational frequency of the cantilevered element, at 406. The indication may be provided via a second capacitive plate. The second capacitive plate may be spaced from and capacitively coupled to the cantilevered element. For example, the indication may be the indication 144 provided by the second capacitive plate 116 of FIG. 1, the indication 244 provided by the second capacitive plate 216 of FIG. 2, or the indication 246 provided by the fourth capacitive plate 218 of FIG. 2, as described above. In a particular embodiment, the indication may be a current having a frequency associated with a vibrational frequency of the cantilevered element.

The method 400 may include amplifying the indication, at 408. For example, the indication may be amplified by an amplifier, such as a gain element associated with a sensor. The amplifier may be the amplifier 140 of FIG. 1, the amplifier 240 of FIG. 2, or the amplifier 242 of FIG. 2, as described above.

In a particular embodiment, the method 400 may further include measuring the frequency of the indication, at 410. The method 400 may also include determining a value associated with the measured frequency of the indication, at 412. For example, a sensor or a sensor device, such as the sensor 100 of FIG. 1 or the sensor device 200 including the sensor array 201 of FIG. 2, may measure the frequency of the indication and determine the value associated with the measured frequency of the indication, as described above.

In another embodiment, instead of or in addition to measuring the frequency of the indication, the method 400 may include detecting a change in the frequency of the indication, at 414. The method 400 may further include determining a value associated with a detected change in frequency of the indication, at 416. For example, a sensor or a sensor device, such as the sensor 100 of FIG. 1 or the sensor device 200 including the sensor array 201 FIG. 2, may detect a change in the frequency of the indication, as described above.

The method 400 may further include outputting the value associated with the measured frequency and/or the value associated with the detected change in the frequency, at 418. For example, the outputted value associated with the measured frequency or the outputted value associated with the detected change in the frequency may be the output 160 of the frequency counter 130 of FIG. 1, the output 260 of the first frequency counter 230 of FIG. 2, or the output 262 of the second frequency counter 232 of FIG. 2.

The method 400 may further include converting the outputted value to a digital value, at 420. For example, the microcomputer interface 227 may convert each sensor output of the sensor array 201 into the digital output 229 (via at least the analog to digital converter 231) of FIG. 2, as described above.

The method 400 may further include processing the digital value, at 422. For example, the digital output 229 may be processed by the microcomputer 280 of FIG. 2, and may be communicated via the wireless modem 290 and the antenna 292 of FIG. 2 to a remote destination, such as the computer server 310, which is remote from one or more sensor devices 301 as shown in FIG. 3. Additionally, the digital values may be received by the computer server 310 and processed by the manager 313 or the processor 320 of FIG. 3. For example, the analytics 314 of the computer of the manager 313 within the computer server 310 may receive and process the digital values produced as a result of the method 400.

The method 400 provides a scheme for operating a sensor or a sensor device to provide data that enables a device remote for the sensor or the sensor device to identify a presence of a particular trigger proximate to the sensor or the sensor device. In response to identification of the particular trigger, a targeted alert may be issued by an alert system to an individual. Accordingly, the individual may be made aware of the particular triggers and take preventative or corrective action to avoid and prevent onset of a respiratory attack caused by the particular trigger.

Figure 5:
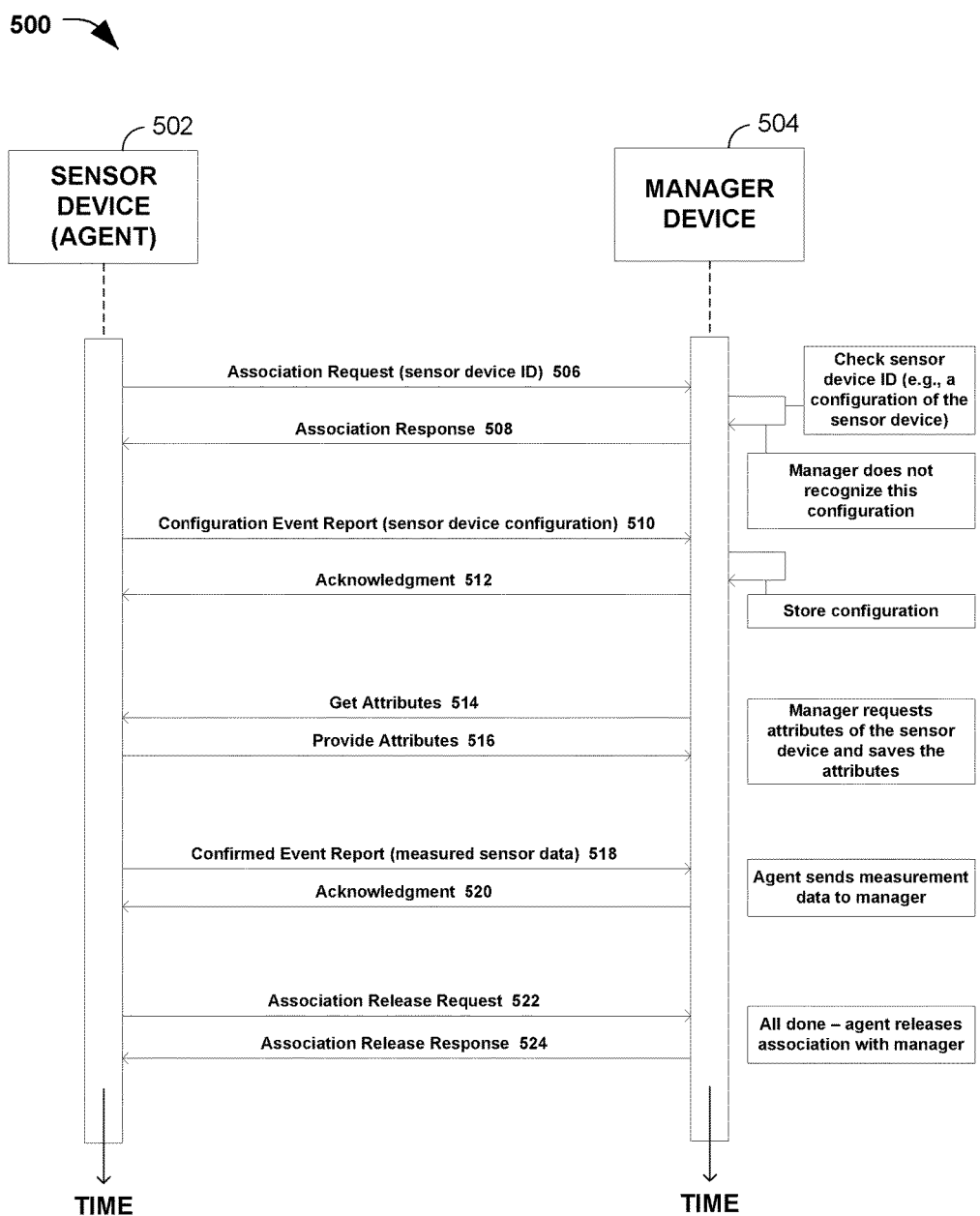
FIG. 5 is a ladder diagram to illustrate a first method of communicating between a sensor device and a manager device.

Referring to FIG. 5, a particular illustrative embodiment of a method 500 of communicating between a representative sensor 502 and a representative manager device 504 is shown. The method 500 is illustrated by a ladder diagram and includes the sensor device 502 and the manager device 504. In a particular illustrative embodiment, the sensor device 502 may include the sensor 100 of FIG. 1, may be the sensor device 200 of FIG. 2, or may be the sensor device 301 of FIG. 3. The manager device 504 may be a processor executing manager software or a manager component, such as the manager 313 of the computer server 310 of FIG. 3. The sensor device 502 is remotely located from the manager device 504 and may communicate via a network with the manager device 504.

In a particular illustrative embodiment, the sensor device 502 may send an association request 506 to the manager device 504. For example, the association request may be used to send a sensor device identifier (ID) of the sensor device 502 to the manager device 504. The manager device 504 may evaluate the sensor device ID and may send an association response 508 to the sensor device 502. In a particular embodiment, the manager device 504 may not recognize the sensor device ID and the association response 508 may indicate an unknown configuration since the sensor device ID has not been identified. In response to receiving the association response 508, the sensor device 502 may communicate a configuration event report 510 to the manager device 504. The configuration event report 510 may include configuration information (e.g. objects) related to the sensor device 502. The configuration event report 510 may be received and evaluated by the manager device 504. In response, the manager device 504 may send an acknowledgement 512, and the manager device 504 may store configuration data including the attributes of the sensor device 502.

After receiving the acknowledgement 512, the sensor device 502 may receive a get attribute command, at 514, from the manager device 504. For example, the manager device 504 may request attributes from the sensor device, and upon receiving the attributes, the manager device 504 saves the attributes received from the sensor device 502. The attributes may be provided by a provide attribute message 516 from the sensor device 502 to the manager device 504.

After receiving the attributes, via the provide attribute message 516, and saving the attributes, the manager device 504 may receive a confirmed event report 518 from the sensor device 502. The confirmed event report 518 may include measured sensor data generated by the sensor device 502. For example, an agent within the sensor device 502 may send data indicating one or more measurements made by the sensor device 502 via the confirmed event report 518 to the manager device 504. The confirmed event report 518 may be acknowledged by an acknowledgement 520 sent by the manager device 504 to the sensor device 502. After the manager device 504 receives the measurement data from the sensor device 502, the communication link between the agent of sensor device 502 and the manager device of 504 may be released (e.g., by the sensor device 502 sending an association release request 522 and by the manager device 504 responding with the association release response 524). Thus, the method 500 provides a communication protocol and a method of communicating between an agent within a sensor device and a manager, such as a manager within a computer server. While a particular sensor device 502 has been shown, it should be understood that one or more sensor devices may communicate with a manager using the protocol of FIG. 5.

Figure 6:
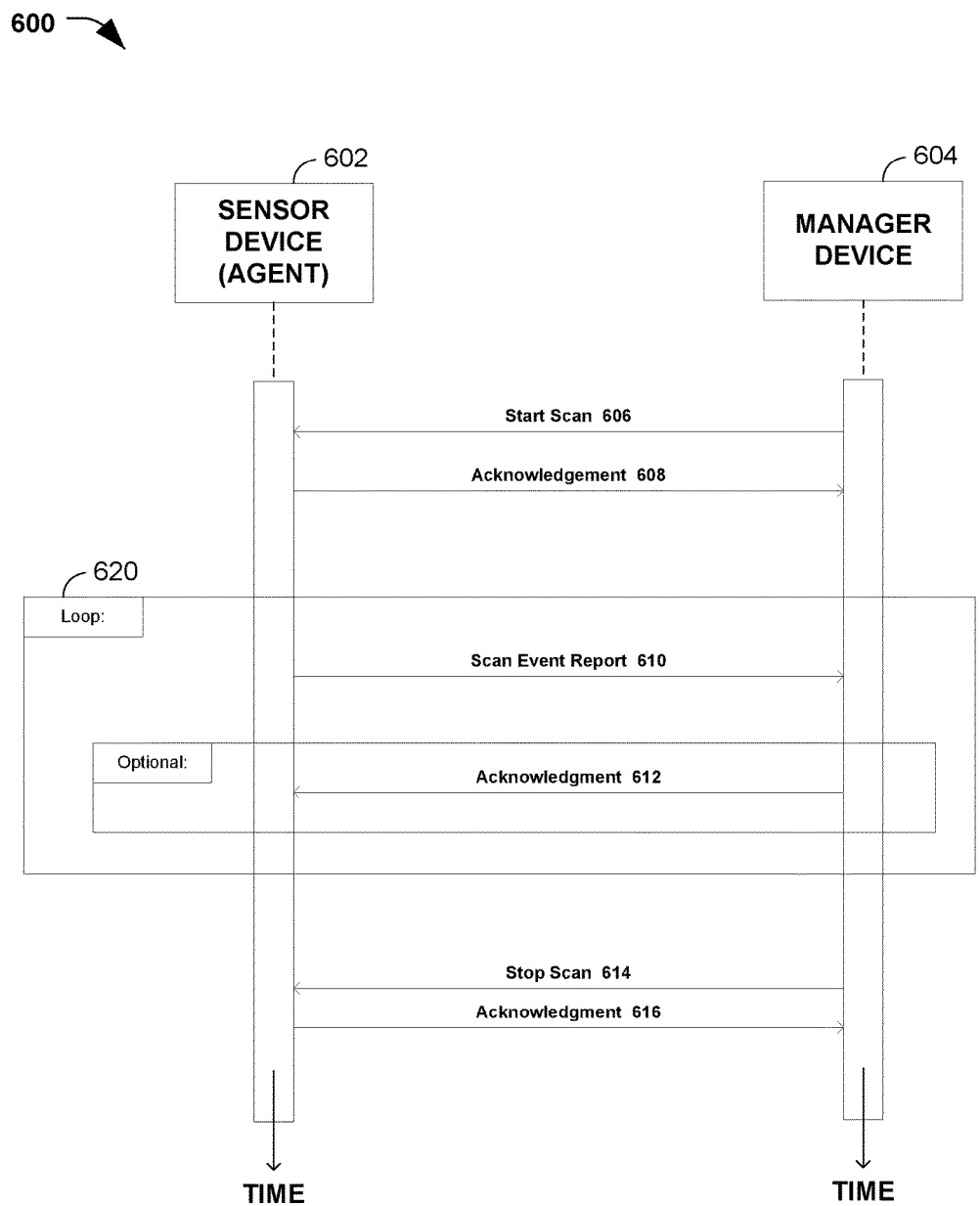
FIG. 6 is a ladder diagram to illustrate a second method of communicating between a sensor device and a manager device.

Referring to FIG. 6, a particular illustrative embodiment of a method 600 of communicating between a representative sensor device 602 and a representative manager device 604 is shown. The method 600 is illustrated by a ladder diagram and includes the sensor device 602 and the manger device 604. The sensor device 602 includes an agent. The sensor device 602 may correspond to the sensor device 200 of FIG. 2, the sensor device 301 of FIG. 3, or the sensor device 502 of FIG. 5. The manager device 604 may be the manager 313 within the computer server 310 of FIG. 3, the manager device 504 of FIG. 5, or another manager within another computing device.

The manager device 604 may send a start scan message 606 to the sensor device 602. In response, the sensor device 602 may send an acknowledgement 608 which may be received by the manager device 604. Thereafter, the sensor device 602 may perform a loop 620 in which the sensor device 602 sends scan event reports 610 and may iterate and send additional scan event reports 610 over a period of time to the manager device 604. Optionally, the manager device 604 may send an acknowledgement 612. The acknowledgement 612 may be sent in response to each scan event report 610 or may be sent once for a predetermined number of scan event reports 610 or when a designated set of scan event reports 610 are received by the manager device 604.

The manager device 604 may stop the scan by sending a stop scan message 614 which may be acknowledged by the sensor device 602 sending an acknowledgement 616 to the manager device 604. Subsequently, scan processing is completed. Thus, the method of communicating between a manager device 604 and a sensor device 602 is shown which includes starting a scan, triggering and receiving scan event reports including measured sensor device data, and stopping of scanning.

Figure 7:
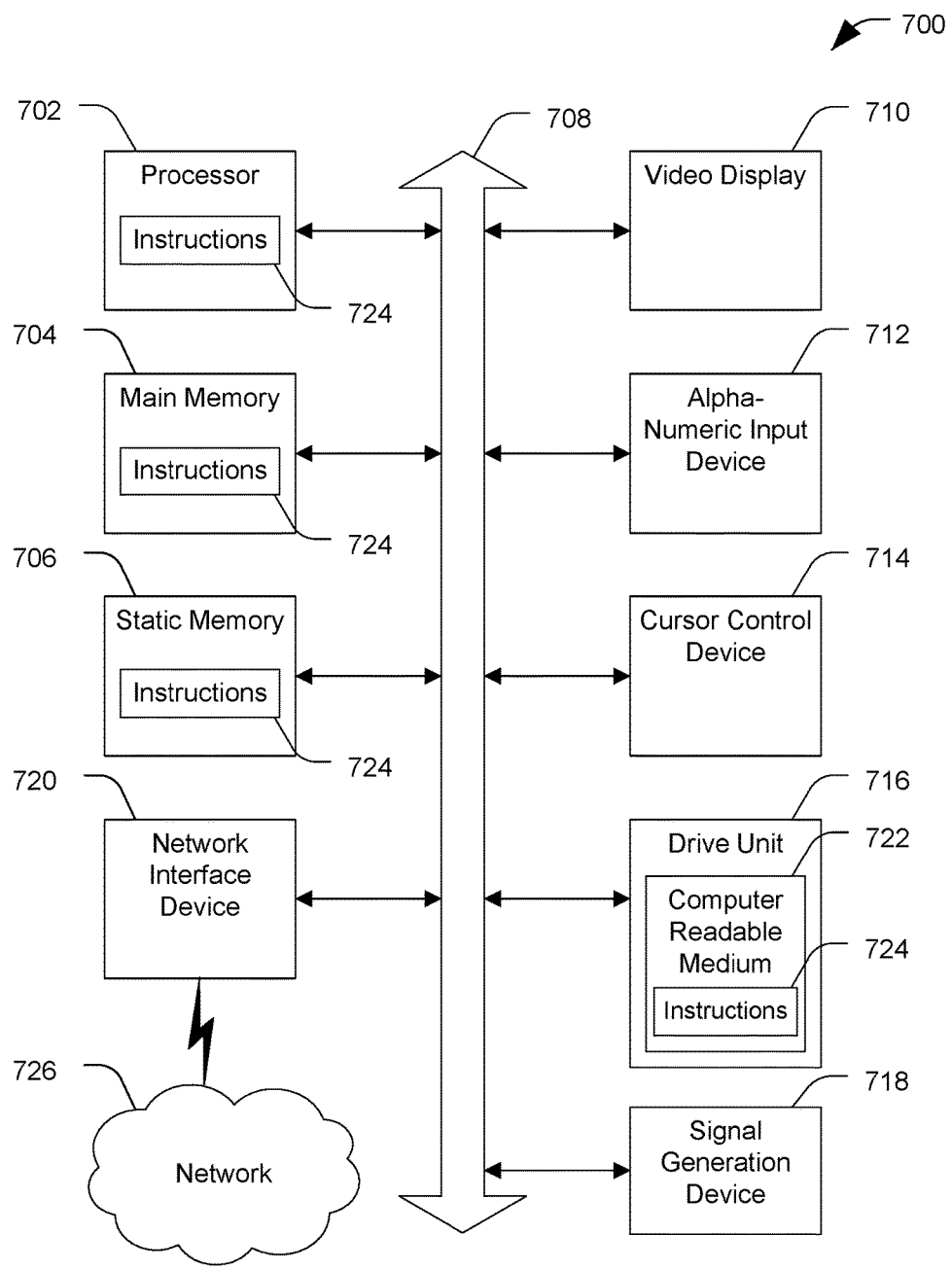
FIG. 7 is a diagram of an illustrative embodiment of a general computer system operable to support embodiments of the systems and methods of FIGS. 1-6.

Referring to FIG. 7, an illustrative embodiment of a general computer system is shown and designated 700. The computer system 700 includes a set of instructions that can be executed to cause the computer system 700 to perform any one or more of the methods or computer based functions disclosed herein. The computer system 700, or any portion thereof, may operate as a standalone device or may be connected, e.g., using a network, to other computer systems or peripheral devices. The computer system 700, or one or more components or subsystems thereof, may be used to implement or may be implemented within one or more other devices described herein. For example, the computer system 700, or components or subsystems thereof, may be used to implement or may be implemented within the microcomputer 280 within the sensor device 200 of FIG. 2 or within the sensor device 301, the computer server 310, the caregiver device 350, the facility control system 354, the access terminal 352, the facility control system 354 of the system 300 of FIG. 3, components thereof, or any combination thereof. In addition, various methods described herein, such as the methods 400, 500, 600 of FIGS. 4-6 may be implemented by a processor, such as the processor 702 of the computer system 700. Thus, the computer system 700, or components thereof, may be used to implement or may be implemented within various other components as described herein and may perform methods and other functionality as described.

The computer system 700 can also be implemented as or incorporated into various other devices, such as a personal computer (PC), a tablet PC, a personal digital assistant (PDA), a mobile device, a palmtop computer, a laptop computer, a desktop computer, a communications device, a web appliance, or any other machine capable of executing a set of instructions (sequential or otherwise) that specify actions to be taken by that machine. In a particular embodiment, the computer system 700 can be implemented using electronic devices that provide audio, video, or data communication. Further, while a single computer system 700 is illustrated, the term "system" shall also be taken to include any collection of systems or sub-systems that individually or jointly execute a set, or multiple sets, of instructions to perform one or more computer functions.

As illustrated in FIG. 7, the computer system 700 may include a processor 702, e.g., a central processing unit (CPU), a graphics-processing unit (GPU), or both. Moreover, the computer system 700 can include a main memory 704 and a static memory 706 that can communicate with each other via a bus 708. In an illustrative embodiment, one or more of the main memory 704 and the static memory 706 may store the manager 313, the database 312, the analytics 314, the alert system 316, the facility control system interface 318, or the agent 305 of FIG. 3.

As shown, the computer system 700 may further include or be coupled to the video display unit 710, such as a liquid crystal display (LCD), an organic light emitting diode (OLED), a flat panel display, a cathode ray tube (CRT) display, a solid-state display, a projection display, a three dimensional display, or a combination thereof. Additionally, the computer system 700 may include an input device 712, such as a keyboard, a remote control device, and a cursor control device 714. The computer system 700 can also include a disk drive unit 716, a signal generation device 718, such as remote control device, and a network interface device 720. Depending on configuration, one or more components of the computer system 700 may not be included. For example, when the computer system 700 or components thereof are used to implement the sensor device 200 of FIG. 2 or the sensor device 301, the computer server 310, the caregiver device 350, the facility control system 354, the access terminal 352, or the facility control system 354 of the system 300 of FIG. 3, one or more of the display unit 710, the input device 712, and the cursor control device 714 may not be included. Alternately, when the computer system 700 or components thereof are used to implement one or more of the sensor device 200 of FIG. 2 or the sensor device 301, the computer server 310, the caregiver device 350, the facility control system 354, the access terminal 352, or the facility control system 354 of the system 300 of FIG. 3, one or more of the display unit 710, the input device 712, and the cursor control device 714 may be included within the client device or may be coupled to the client device.

In a particular embodiment, as depicted in FIG. 7, the disk drive unit 716 may include a tangible (i.e., non-transitory) computer-readable medium 722 in which one or more sets of instructions 724, e.g., software, can be embedded. Further, the instructions 724 may embody one or more of the methods or logic as described herein. To illustrate, the instructions may embody the methods 400, 500, 600 of FIGS. 4-6, or any combination thereof. In a particular embodiment, the instructions 724 may reside completely, or at least partially, within the main memory 704, the static memory 706, and/or within the processor 702 during execution by the computer system 700. The main memory 704 and the processor 702 also may include tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit.

In accordance with various embodiments of the present disclosure, the methods described herein may be implemented by software programs executable by the computer system 700. Further, in an exemplary, non-limiting embodiment, implementations can include distributed processing, component/object distributed processing, and parallel processing. Alternatively, virtual computer system processing can be constructed to implement one or more of the methods or functionality as described herein.

The present disclosure contemplates a tangible computer-readable medium that includes instructions 724 or receives and executes instructions 724, so that a device connected to a network 726 can communicate audio, voice, video, or data over the network 726. Further, the instructions 724 may be transmitted or received over the network 726 via the network interface device 720. For example, the instructions 724 may be stored at the memory 284 of FIG. 2, the memory 322 of FIG. 3 or a particular memory included in any one of the sensor device 301, the computer server 310, the caregiver device 350, the facility control system 354, the access terminal 352, or the facility control system 354 of the system 300 of FIG. 3.

The term "computer-readable medium" or "processor-readable medium" may include a single medium or multiple media, such as a centralized or distributed database, and/or associated caches and servers that store one or more sets of instructions. The term "computer-readable medium" or "processor-readable medium" may refer to any non-transitory, tangible medium that is capable of storing or encoding a set of instructions 724 for execution by the processor 702 or that cause the computer system 700 to perform any one or more of the methods or operations disclosed herein.

In a particular non-limiting, exemplary embodiment, the computer-readable medium can include a solid-state memory, such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device. Accordingly, the disclosure is considered to include any one or more of a computer-readable storage medium and other equivalents and successor media, in which data or instructions may be stored.

Software (e.g., the instructions 724) that implement the disclosed methods may be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories.

Although the present specification describes components and functions that may be implemented in particular embodiments with reference to particular standards and protocols, the disclosure is not limited to such standards and protocols. For example, standards for Internet, other packet switched network transmission (e.g., TCP/IP, UDP/IP, HTTP, Wi-Fi, IEEE 802.11, IEEE 802.15, IEEE 11073), systems operating within any RF spectrum bands, and standards for encoding data represent examples of the state of the art. Such standards may occasionally be superseded by faster or more efficient equivalents having substantially the same functions. Accordingly, replacement standards and protocols having the same or similar functions as those disclosed herein are considered equivalents thereof.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above-disclosed subject matter is to be considered illustrative, and not restrictive, and the appended claims are intended to cover all such modifications, enhancements, and other embodiments, which fall within the scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method comprising:
receiving, at a computing device, multiplexed sensor data from a sensor array, the multiplexed sensor data including first data from a first sensor of the sensor array and second data from a second sensor of the sensory array, the first data including first frequency information of a first cantilevered element, the first cantilevered element including a coating material having an affinity for a compound and no diffusion barrier, and the second data including second frequency information of a second cantilevered element, the second cantilevered element including the coating material and a diffusion barrier, wherein the diffusion barrier inhibits mass transfer to the second cantilevered element; and
conditionally generating, by the computing device based on an analysis of the first data and the second data, an output, the output conditioned on the first frequency information and the second frequency information indicating more than a threshold amount of the compound present at the sensor array.

2. The method of claim 1, further comprising:
before receiving the multiplexed sensor data, sending a scan start command to the sensor array, wherein the multiplexed sensor data is received in response to the scan start command; and
after receiving the multiplexed sensor data, sending a stop scan command to the sensor array, wherein the sensor array ceases transmitting sensor data based on the stop scan command.

3. The method of claim 1, further comprising sending the output to a facility control system, wherein the output enables the facility control system to implement a command associated with presence of the compound.

4. The method of claim 3, wherein the command adjusts operation of a ventilation system.

5. The method of claim 1, further comprising sending the output to a caretaker device.

6. The method of claim 1, further comprising sending the output to a device associated with a person susceptible to respiratory distress due to presence of the compound.

7. The method of claim 1, wherein the multiplexed sensor data includes location data indicating a location of the sensor array.

8. The method of claim 1, wherein the first cantilevered element is an element of a micro-electromechanical system.

9. The method of claim 1, wherein the second cantilevered element is an element of a micro-electromechanical system.

10. The method of claim 1, wherein the computing device uses the second data to adjust the first data for vibrations due to temperature of the sensor array.

11. An apparatus comprising:
a communication interface configured to receive multiplexed sensor data from a sensor array, the multiplexed sensor data including first data from a first sensor of the sensor array and second data from a second sensor of the sensory array, the first data including first frequency information of a first cantilevered element, the first cantilevered element including a coating material having an affinity for a compound and no diffusion barrier, and the second data including second frequency information of a second cantilevered element, the second cantilevered element including the coating material and a diffusion barrier, wherein the diffusion barrier inhibits mass transfer to the second cantilevered element; and
a processor configured to analyze the first data and the second data and to conditionally generate an output, the output conditioned on the first data and the second data indicating more than a threshold amount of the compound at the sensor array.

12. The apparatus of claim 11, further comprising a database to store the multiplexed sensor data.

13. The apparatus of claim 11, wherein the multiplexed sensor data includes information indicating a location of the sensor array.

14. The apparatus of claim 11, wherein the multiplexed sensor data includes third data from a third sensor configured to detect a different compound.

15. The apparatus of claim 11, wherein the compound is a volatile organic compound, a particulate, or both.

16. A computer-readable storage device storing instructions executable by a processor to cause the processor to perform operations, the operations comprising:
receiving sensor data from sensors of a sensor array, the sensor data including first data from a first sensor of the sensor array and second data from a second sensor of the sensor array, the first data including first frequency information of a first cantilevered element, the first cantilevered element including a coating material having an affinity for a compound and no diffusion barrier, and the second data including second frequency information of a second cantilevered element, the second cantilevered element including the coating material and a diffusion barrier, wherein the diffusion barrier inhibits mass transfer to the second cantilevered element;
multiplexing the sensor data from the sensors to produce multiplexed sensor data; and
transmitting the multiplexed sensor data to a receiver.

17. The computer-readable storage device of claim 16, wherein the multiplexed sensor data identifies the sensor array and a location of the sensor array.

18. The computer-readable storage device of claim 16, wherein the first sensor includes a frequency counter to determine a frequency of a signal induced in a first capacitive plate by vibration of the first cantilevered element.

19. The computer-readable storage device of claim 18, wherein the first sensor includes a second capacitive plate configured to induce vibration of the first cantilevered element.

20. The computer-readable storage device of claim 16, wherein the second data enables adjustment of the first data to compensate for temperature of the sensor array.

* * * * *